（12） United States Patent
Nath et al.

(10) Patent No.: US 11,548,839 B2
(45) Date of Patent: Jan. 10, 2023

(54) INTEGRATED OXIDATIVE ALKANE DEHYDROGENATION AND HYDROGEN GENERATION PROCESS

(71) Applicant: INDIAN OIL CORPORATION LIMITED, Maharashtra (IN)

(72) Inventors: Vineeth Venu Nath, Faridabad (IN); Hima Bindu Doosa, Faridabad (IN); Ram Mohan Thakur, Faridabad (IN); Saravanan Subramani, Faridabad (IN); Sahithi Ravuluri, Faridabad (IN); Madhusudan Sau, Faridabad (IN); Gurpreet Singh Kapur, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/478,767

(22) Filed: Sep. 17, 2021

(65) Prior Publication Data
US 2022/0081375 A1 Mar. 17, 2022

(30) Foreign Application Priority Data
Sep. 17, 2020 (IN) .............................. 202021040369

(51) Int. Cl.
*B01D 53/047* (2006.01)
*C01B 3/26* (2006.01)
*C01B 3/56* (2006.01)
*C07C 5/48* (2006.01)
*C07C 7/00* (2006.01)
*C07C 7/04* (2006.01)

(52) U.S. Cl.
CPC .............. *C07C 5/48* (2013.01); *B01D 53/047* (2013.01); *C01B 3/26* (2013.01); *C01B 3/56* (2013.01);
(Continued)

(58) Field of Classification Search
CPC .............. C01B 3/56; C01B 2203/1235; C01B 2203/0233; C01B 2203/062;
(Continued)

(56) References Cited

U.S. PATENT DOCUMENTS 3,513,215 A * 5/1970 Ogle ...................... C07C 11/00
585/901
4,788,371 A 11/1988 Imai et al.
(Continued)

FOREIGN PATENT DOCUMENTS

RU          2702895 C1   10/2019
WO    WO 2007 018 518 A1 * 2/2007 ................. F25J 3/02
(Continued)

*Primary Examiner* — Timothy C Vanoy
(74) *Attorney, Agent, or Firm* — Maschoff Brennan (57) ABSTRACT

As part of an integrated oxidative alkane dehydrogenation and hydrogen generation process, carbon dioxide from Pressure Swing Adsorption (PSA) off gas stream of Hydrogen Generation Unit (HGU), and alkane from any known source are sent to oxidative dehydrogenation (ODH) unit for producing high value olefins, such as ethylene, propylene and butenes. Products formed from ODH reactor are separated and the stream comprising of hydrogen, carbon monoxide and methane are recycled to Shift reactor of HGU unit for enhanced production of hydrogen at PSA.

9 Claims, 2 Drawing Sheets (52) U.S. Cl.
CPC ............... *C07C 7/005* (2013.01); *C07C 7/04* (2013.01); *B01D 2256/16* (2013.01); *B01D 2257/502* (2013.01); *B01D 2257/504* (2013.01); *B01D 2257/7025* (2013.01); *C01B 2203/0233* (2013.01); *C01B 2203/042* (2013.01); *C01B 2203/062* (2013.01); *C01B 2203/1235* (2013.01)

(58) Field of Classification Search
CPC ... C01B 2203/042; C01B 3/26; B01D 53/047; B01D 2257/7025; B01D 2257/502; C07C 5/48; C07C 7/005; C07C 7/04
See application file for complete search history.

(56) References Cited

U.S. PATENT DOCUMENTS

| | | | |
|---|---|---|---|
| 5,527,979 | A | 6/1996 | Agaskar et al. |
| 6,326,523 | B1 | 12/2001 | Stahl et al. |
| 6,518,476 | B1 | 2/2003 | Culp et al. |
| 7,041,271 | B2 | 5/2006 | Drnevich et al. |
| 7,094,942 | B2 | 8/2006 | Abdulwahed et al. |
| 7,744,829 | B2 | 6/2010 | Brophy et al. |
| 8,519,210 | B2 | 8/2013 | Arnold et al. |
| 9,545,610 | B2 | 1/2017 | Simanzhenkov et al. |
| 9,993,798 | B2 | 6/2018 | Simanzhenkov et al. |
| 10,058,850 | B2 | 8/2018 | Sanchez Valente et al. |
| 10,357,754 | B2 | 7/2019 | Simanzhenkov et al. |
| 2009/0312591 | A1 | 12/2009 | Schubert et al. |
| 2019/0194092 | A1 | 6/2019 | Doosa et al. |
| 2021/0291150 | A1* | 9/2021 | Karakaya ................ B01J 23/26 |

FOREIGN PATENT DOCUMENTS

| | | | | |
|---|---|---|---|---|
| WO | 2018037315 A | 3/2018 | | |
| WO | WO 2018 219 996 A1 * | 12/2018 | ............... | C07C 7/11 |
| WO | WO 2019 175 731 A1 * | 9/2019 | ............... | C07C 5/48 |

* cited by examiner

INTEGRATED OXIDATIVE ALKANE DEHYDROGENATION AND HYDROGEN GENERATION PROCESS

FIELD OF THE INVENTION

The present invention discloses an integrated process for producing light olefins selectively through Oxidative Dehydrogenation (ODH) of light alkanes, wherein a hydrocarbon stream consisting of light alkanes such as ethane, propane, butane or any mixture thereof, are converted to high value light olefins such as ethylene, propylene, butene by catalytic oxidative dehydrogenation using carbon dioxide from the off gas stream of Pressure Swing Adsorption (PSA) unit of Hydrogen Generation Unit (HGU).

BACKGROUND OF THE INVENTION

On purpose light olefin production technologies such as propane dehydrogenation have gained momentum in the recent past due to the increased demand of light olefins that are used as petrochemical feedstock. This trend has further strengthened production of propylene and butene since the conventional technologies such as steam cracking favor production of ethylene. A handful of commercial processes are available for alkane dehydrogenation; however, the oxidative dehydrogenation route is not common.

U.S. Pat. No. 7,094,942 B2 describes an oxidative dehydrogenation process for converting alkane into alkene using a chromium-based dehydrogenation catalyst which comprises of 12 wt % to 18 wt % chromium in presence of carbon dioxide at a temperature of 400° C. to 700° C. and at a pressure of 0.1-10 atm.

U.S. Pat. No. 4,788,371A describes an oxidative dehydrogenation process of a dehydrogenatable hydrocarbon, using a noble metal catalyst, utilizing steam and an oxygen containing gas in a reaction zone at conditions sufficient to promote both oxidation and dehydrogenation reactions.

U.S. Pat. No. 6,326,523 B1 describes the process for the dehydrogenation of a hydrocarbon feed, where the hydrocarbon feed is dehydrogenated, and hydrogen formed during reaction is removed by its oxidation with a redox oxide. The dehydrogenation and hydrogen removal steps are performed simultaneously, using a dehydrogenation catalyst combined with a metal phosphate; thereby higher overall conversion and selectivity are achieved for the dehydrogenation process.

U.S. Pat. No. 6,518,476 B1 describes methods for manufacturing olefins such as ethylene and propylene from lower alkanes, that is, methane, ethane and/or propane, by oxidative dehydrogenation at elevated pressure. The olefins are selectively recovered from unconverted lower alkane feed and reaction byproducts by using complexation separation, such as an absorption separation that uses aqueous silver nitrate as the complexation agent.

U.S. Pat. No. 5,527,979 describes a process for converting alkane to alkene where the alkane feed is dehydrogenated by a dehydrogenation catalyst in the first reactor, and the effluent from the first reactor, along with oxygen, is then passed into a second reactor containing a metal oxide catalyst where the selective combustion of hydrogen is catalyzed. The dehydrogenation catalyst comprises platinum and the oxidation catalyst contains bismuth, antimony, indium, or molybdenum or their mixture.

U.S. Pat. No. 9,993,798 B2 describes an integrated process consisting of a steam cracker where an oxidative dehydrogenation unit is placed upstream and/or downstream of $C_2$ splitter for enhancing ethylene production.

US20190194092A1 (RU 2702895) describes an integrated process for enhancing the yields of propylene and other light olefins in FCC process by integrating FCC with OPDH process where the feed for OPDH process are propane from FCC $C_3$ splitter and carbon dioxide from FCC flue gas. The product stream from OPDH reactor is routed to Gas-con section of FCC such that higher propylene and ethylene yields are achieved from the integrated process.

U.S. Pat. No. 7,041,271B2 relates to a method in which natural gas is injected into the separated light ends prior to the treatment thereof to produce hydrogen.

WO2018037315A concerns in integrated process of a photocatalytic water splitting process and oxidative dehydrogenation of ethane process to produce hydrogen and ethylene.

US20090312591A1 relates to a process for preparing propene from propane. Here propane and, optionally, steam and an oxygenous gas stream is send to a dehydrogenation zone and from the product gases, propylene is selectively removed from propane by selective adsorption.

U.S. Pat. No. 9,545,610B2 and U.S. Ser. No. 10/357,754B2 relates to integration of oxidative dehydrogenation process with steam cracker for conversion of ethane to ethylene.

U.S. Pat. No. 7,744,829B2 relates to an apparatus for oxidative dehydrogenation of hydrocarbon.

U.S. Pat. No. 8,519,210B2 relates to a process for the oxidative dehydrogenation of ethane to ethylene, where ethane and oxygen-containing gas is contacted in the presence of at least one of water and steam and an oxidative dehydrogenation catalyst comprising $Mo_aV_bNb_cY_dTe_eO_n$ wherein Y=Sb or Ni; a=1.0; b=0.05 to 1.0; c=0.001 to 1.0; d=0.001 to 1.0; e=0.001 to 0.5; and n is determined by the oxidation states of the other elements. The product stream is contacted with an oxygen elimination catalyst in an oxygen elimination reaction zone to combust at least a portion of the oxygen and followed by separation of water, carbon dioxide, unreacted ethane and ethylene.

U.S. Ser. No. 10/058,850B2 relates to the oxidative dehydrogenation of light paraffins using a tellurium-free multimetallic oxide catalyst. More particularly, it relates to preparation of highly active and selective catalysts for the oxidative dehydrogenation of ethane to produce ethylene at moderate temperatures, <500° C., without the formation of acetic acid and/or other oxygenated hydrocarbons.

The prior art mentioned above suffer from the drawback of requiring a clean stream of oxidative agent to facilitate oxidative dehydrogenation process and carbon dioxide is preferred due to its mild oxidation activity. The major sources for carbon dioxide in refineries are flue gases from furnaces and FCC regenerator that have a concentration of carbon dioxide in the range of 10-30 wt %. However, flue gas stream has oxygen (1-5 wt %) present in it that hinders its use in an ODH process. This calls for a separation step to purify carbon-dioxide from the flue gas streams before utilizing it in an ODH process. The present invention utilizes the PSA off gas stream from Hydrogen Generation Unit (HGU) as a carbon dioxide source. The PSA off-gas stream has atypical composition of carbon dioxide in the range of 80 wt %-95 wt % and rest hydrogen, methane, carbon monoxide and steam. This stream can directly be routed to the ODH process due to higher concentration of carbon dioxide and absence of oxygen, thereby eliminating a separation process.

The ODH process utilizing carbon dioxide, converts alkane to alkene and produces water and carbon monoxide as by products because of the reaction of hydrogen with carbon dioxide (reverse water gas shift reaction). This reverse water gas shift reaction helps in shifting the equilibrium limited alkane to alkene reaction in the forward direction. However, this reduces the potential of hydrogen production from the dehydrogenation process. The integration of ODH with HGU addresses this issue by converting carbon monoxide formed in ODH process to hydrogen by water gas shift reaction in the Shift Reactor of HGU. Thus, the overall hydrogen production potential from the dehydrogenation process remains intact. This integration has an additional advantage that the hydrogen so generated as a part of dehydrogenation reaction is captured as pure hydrogen in PSA unit of HGU, thereby eliminating the requirement of standalone hydrogen separation system.

The present invention has the following advantages over the prior arts:

1. Production of high valued petrochemical feed stocks such as ethylene and propylene by utilizing existing units in the oil refinery;
2. Utilization of carbon dioxide from existing HGU PSA off gas thereby eliminates requirement of additional carbon dioxide purification system;
3. Potential of producing hydrogen from ODH process which otherwise would have been lost as water;
4. Increased production of hydrogen from HGU by recycling CO from ODH reaction;
5. No separate hydrogen separation system requirement; and
6. No separate CO mitigation/conversion system requirement.

Objectives of the Invention

It is a primary objective of the invention to provide an integrated process for producing light olefins selectively through Oxidative Dehydrogenation (ODH) of light alkanes wherein a hydrocarbon stream consisting of light alkanes such as ethane, propane and butane or any mixture thereof, are converted to high value light olefins such as ethylene, propylene and butene by catalytic oxidative dehydrogenation using carbon dioxide from the off gas stream of Pressure Swing Adsorption (PSA) unit of Hydrogen Generation Unit (HGU).

A further objective of the present invention is to produce light olefins with higher selectivity and also significantly increase the production of hydrogen in HGU due to the integration of processes.

Another objective of the present invention is to utilize the carbon dioxide from existing HGU PSA off gas without any treatment/purification.

Yet another objective of the present invention is to increase the fuel value of the carbon dioxide rich stream of HGU PSA off gas by converting carbon dioxide to carbon monoxide through ODH process.

SUMMARY OF THE INVENTION

In an aspect of the present invention, the present invention discloses an integrated process for catalytic oxidative dehydrogenation (ODH) of alkane(s) and for generation of hydrogen, the process comprising: a) feeding fresh hydrocarbon alkane feed (1) along with carbon dioxide rich stream (2) to ODH reactor (A) comprising of dehydrogenation catalyst, where the alkane feed gets converted into alkenes and producing an effluent gas comprising of hydrogen, methane, carbon monoxide, carbon dioxide, water and unreacted alkanes; b) separating ODH effluent gas (5) from the ODH reactor (A) using a Gas Separation system, wherein the Gas Separation system consists of De-Propanizer section (B), De-Butanizer and $C_4$ Splitter section (C), $C_3$ Splitter section (D), De-Methanizer section (E) and $C_2$ Splitter section (F); c) separating the ODH effluent gases (5) into (i) $C_{4+}$ stream (6) consisting of $C_4$ alkanes, $C_4$ olefins and higher hydrocarbons; (ii) $C_3$ stream (7) consisting of propane and propylene; and (iii) Off gas stream (8) consisting of hydrogen, methane, ethane, ethylene, carbon monoxide and carbon dioxide using the De-Propanizer section (B); d) separating butanes (3), butene (9) and heavy hydrocarbons (10) from $C_4$+ stream (6) using the De-Butanizer and $C_4$ Splitter section (C) and recycling back the butane (3) to the ODH reactor (A) for further conversion; e) separating the $C_3$ stream (7) into petrochemical grade propylene (11) and propane rich stream (4) using a $C_3$ Splitter (D) and recycling back propane rich stream (4) to the ODH reactor (A) for further conversion; f) routing the Off gas stream (8) from the De-Propanizer section (B) to De-Methanizer section (E), wherein the Off gas stream (8) gets separated into two streams (i) a stream consisting of ethane, ethylene and carbon dioxide (12) and (ii) a stream consisting of hydrogen, methane and carbon monoxide (13); g) routing the stream consisting of ethane, ethylene and carbon dioxide (12) to the $C_2$-Splitter section (F) wherein the stream (12) is separated into petrochemical grade ethylene (15) and a stream rich in ethane and carbon dioxide (14); h) routing the stream rich in ethane and carbon dioxide (14) back to the ODH reactor (A) for recycling of ethane and carbon dioxide; i) routing the stream (13) coming from the De-Methanizer section (E) consisting of hydrogen, methane and carbon monoxide to Hydrogen Generation Unit (HGU) Shift Reactor (G) and mixing the stream (13) with effluent gases (17) coming from Hydrogen Generation Unit (HGU) Reformer Reactor (H), wherein the HGU Reformer reactor (H) is fed with methane, naphtha or other suitable hydrocarbon feed and steam (16) and the hydrocarbon feed and steam (16) undergo reforming reaction at elevated temperatures of about 750-850° C. and produces effluent gas (17) comprising of hydrogen, carbon monoxide, carbon dioxide and un-reacted methane and steam and traces of nitrogen; j) converting the carbon monoxide from the effluent gases (17) and from the stream (13) into hydrogen and carbon dioxide in presence of steam in the HGU Shift reactor (G); k) routing product gases (18) from the HGU Shift reactor (G) consisting of hydrogen, carbon dioxide and rest carbon monoxide, methane, steam and nitrogen to Pressure Swing Adsorption (PSA) section (I) of HGU to separate pure hydrogen (19); l) routing Off gases from PSA (20) having a composition of carbon dioxide 80-95 wt %, carbon monoxide 0.1-5 wt %, methane 0.1-10 wt %, hydrogen 0.1-5 wt % and traces of steam and nitrogen to furnace of HGU reformer reactor (H) as fuel (21); m) routing a portion of the PSA Off gas (22) to the ODH reactor (A) as a carbon dioxide source to supplement the recycle carbon dioxide rich stream (14) coming from the $C_2$ Splitter section (F).

PSA off gas composition range will cover the cases of "other hydrocarbon feed" used in hydrogen generation unit.

In an embodiment of the present invention, the fresh hydrocarbon alkane feed (1) is selected from the group consisting of ethane, propane, n-butane and iso-butane or any mixture thereof.

In an embodiment of the present invention, the carbon dioxide rich stream (2) is a PSA off gas stream (22).

In an embodiment of the present invention, conversion of the propane to propylene is 20-40 wt % and selectivity of the propylene is 85-95 wt %.

In an embodiment of the present invention, the ODH reactor (A) is a fixed bed tubular reactor or a fluidized bed reactor or a moving bed reactor or any combination thereof.

In an embodiment of the present invention, the dehydrogenation catalyst comprises of metal oxides, wherein metal in the metal oxide is selected from the group consisting of VB, VIB, VIII and alkali metals group.

In an embodiment of the present invention, molar ratio of the fresh hydrocarbon alkane feed (1) to the carbon dioxide rich stream (2) in step a) is in the range of 0.3-0.8.

In an embodiment of the present invention, gas hourly space velocity (GHSV) of a mixture of the fresh hydrocarbon alkane feed (1) and the carbon dioxide rich stream (2) in step a) is 200-2500 $h^{-1}$.

In an embodiment of the present invention, diluent ($N_2$) concentration in a mixture of the fresh hydrocarbon alkane feed (1) and the carbon dioxide rich stream (2) in step a) is 0.01-30 vol %.

DETAILED DESCRIPTION OF THE INVENTION

The present invention utilizes the PSA off gas stream from Hydrogen Generation Unit (HGU) as a carbon dioxide source. The PSA off-gas stream has atypical composition of carbon dioxide in the range of 80 wt %-95 wt % and rest hydrogen, methane, carbon monoxide and steam. This stream can directly be routed to the ODH process due to higher concentration of carbon dioxide and absence of oxygen, thereby eliminating a separation process.

The ODH process utilizing carbon dioxide, converts alkane to alkene and produces water and carbon monoxide as by products because of the reaction of hydrogen with carbon dioxide (reverse water gas shift reaction). This reverse water gas shift reaction helps in shifting the equilibrium limited alkane to alkene reaction in the forward direction. However, this reduces the potential of hydrogen production from the dehydrogenation process. The integration of ODH with HGU addresses this issue by converting carbon monoxide formed in ODH process to hydrogen by water gas shift reaction in the Shift Reactor of HGU. Thus, the overall hydrogen production potential from the dehydrogenation process remains intact. This integration has an additional advantage that the hydrogen so generated as a part of dehydrogenation reaction is captured as pure hydrogen in PSA unit of HGU, thereby eliminating the requirement of standalone hydrogen separation system.

According to the main embodiment, the present invention relates to an integrated oxidative alkane dehydrogenation and hydrogen generation process, wherein the $CO_2$ from Pressure Swing Adsorption (PSA) off gas stream of Hydrogen Generation Unit (HGU), and alkane from any known source are sent to oxidative dehydrogenation (ODH) unit for producing high value olefins, primarily ethylene, propylene and butene and hydrogen and carbon monoxide.

In the detailed embodiment, the ODH reactor effluent is sent to a Gas Separation section wherein ethylene, propylene and butene are separated and purified, and the off-gas stream comprising of hydrogen, methane and carbon monoxide is routed to Shift reactor of HGU wherein carbon monoxide is further converted to carbon dioxide and hydrogen in the presence of steam. This integration not only produces light olefins from their respective alkane by ODH process but also enhances the hydrogen production from HGU.

In this process for the production of light olefins with high selectivity through oxidative dehydrogenation (ODH) of light hydrocarbons, a hydrocarbon stream consisting of light alkanes such as ethane, propane and butane or a mixture thereof are converted to high value $C_2$, $C_3$ and $C_4$ olefins by catalytic oxidative dehydrogenation using carbon dioxide. The reactor used for ODH process can be a fixed bed tubular reactor or a fluidized bed reactor or a moving bed reactor or any combination thereof. The dehydrogenation catalyst comprises of metal oxides selected from metals of groups, VB, VIB, VIII and alkali metals. The source of carbon dioxide is Pressure Swing Adsorption (PSA) off gas stream of Hydrogen Generation Unit (HGU). The PSA off gas stream has a typical composition of carbon dioxide in the range of 80 wt %-95 wt % and rest hydrogen, methane, carbon monoxide and steam. This stream can directly be routed to the ODH process, due to higher concentration of carbon dioxide and absence of oxygen, without any separation process.

The product stream from ODH reactor containing $C_2$, $C_3$ and $C_4$ olefins along with unconverted ethane, propane, butane, and other gases are routed to Gas Separation section where light olefins are separated. The off gas containing hydrogen, methane and carbon monoxide from the Gas Separation section is sent to the Shift Reactor of HGU. The carbon monoxide is thus converted into hydrogen and carbon dioxide in presence of steam in the Shift Reactor. The hydrogen so produced is separated in the PSA and the off-gas lean in hydrogen is recycled back to the ODH reactor. Further, a gas stream containing ethane and carbon dioxide are separated from the ODH product gases in the Gas Separation section and sent back to the ODH reactor as recycle. Unconverted propane and butanes are also separated in the Gas Separation section and recycled back to the ODH reactor.

Process Description

Figure 1:
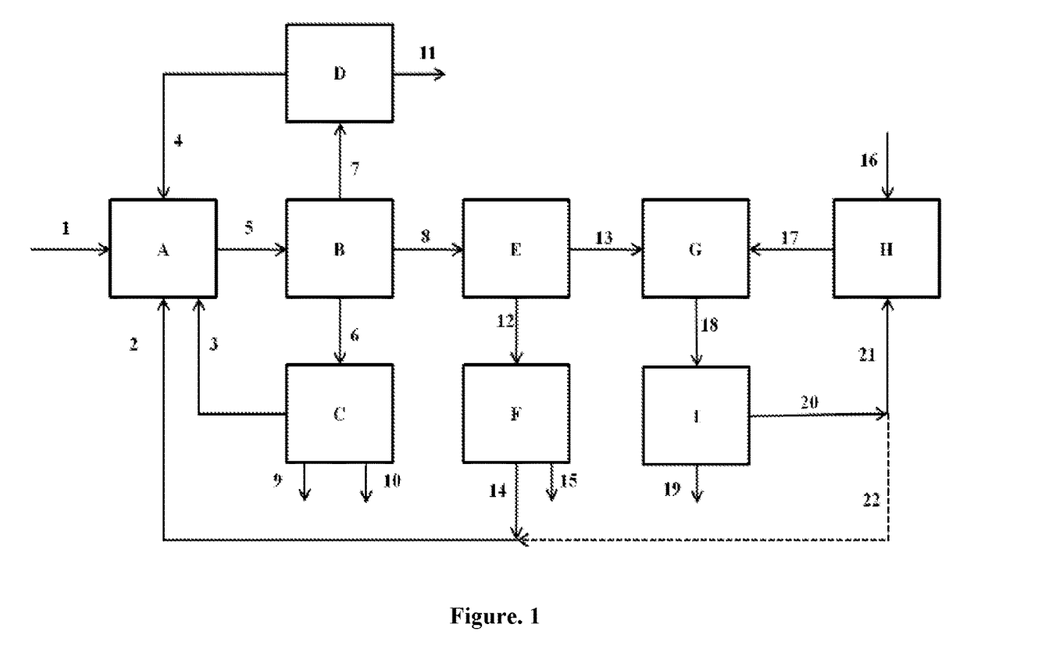
FIG. 1: illustrates the schematic representation of process of the present invention for oxidative dehydrogenation of alkane.

Fresh hydrocarbon alkane feed such as ethane, propane, n-butane and iso-butane or any mixture thereof (1) along with carbon dioxide rich stream (2) are sent to the ODH reactor (A) where the alkanes get converted into alkenes along with minor quantities of other gases such as hydrogen, methane etc. The carbon dioxide acts as a mild oxidizing agent and favors the dehydrogenation reaction. The PSA off gas stream from HGU has a typical composition of carbon dioxide 80-95 wt %, carbon monoxide 0.1-5 wt %, methane 0.1-10 wt %, hydrogen 0.1-5 wt %, and traces of steam and nitrogen (from reformer feed). Thus, the HGU off gas stream is the best suited source of carbon dioxide for ODH process due to high concentration of carbon dioxide and absence of oxygen. Hydrogen and methane in HGU off gas is also helpful in regulating the oxidation state of metals in the catalyst favoring higher alkene selectivity.

The effluent gas (5) from the ODH reactor is sent to the Gas Separation system. The Gas Separation system consists of De-Propanizer section (B), De-Butanizer and $C_4$ Splitter section (C), $C_3$ Splitter section (D), De-Methanizer section (E) and $C_2$ Splitter section (F). The De-Propanizer section (B) separates the ODH effluent gases (5) into the following:
  (i) $C_4$+ stream (6) consisting of $C_4$ alkanes, $C_4$ olefins and higher hydrocarbons
  (ii) $C_3$ stream (7) consisting of propane and propylene and
  (iii) Off gas stream (8) consisting of hydrogen, methane, ethane, ethylene, carbon monoxide and carbon dioxide.

The $C_4$+ stream (6) is sent to the De-Butanizer and $C_4$ Splitter section (C) wherein butanes (3), butene (9) and heavy hydrocarbons (10) are separated. The butane stream (3) is recycled back to the ODH reactor (A) for further conversion. The $C_3$ stream (7) is further separated into petrochemical grade propylene (11) and propane rich stream (4) in a $C_3$ Splitter (D). The propane rich stream (4) is recycled back to the ODH reactor (A) for its further conversion.

The off gas stream (8) from the De-Propanizer section (B) is sent to De-Methanizer section (E) where this gets separated into two streams (i) a stream consisting of ethane, ethylene and carbon dioxide (12) and (ii) a stream consisting of hydrogen, methane and carbon monoxide (13). The stream consisting of ethane, ethylene and carbon dioxide (12) is sent to the $C_2$-Splitter section (F) where it is separated into petrochemical grade ethylene (15) and a stream rich in ethane and carbon dioxide (14). The stream rich in ethane and carbon dioxide (14) is sent back to the ODH reactor (A) for recycling of ethane and carbon dioxide.

The stream (13) coming from the De-Methanizer section (E) consists of hydrogen, methane and carbon monoxide and is sent to the Shift Reactor of HGU (G). This stream (13) gets mixed with the effluent gases (17) from the HGU Reformer Reactor (H). The HGU Reformer reactor (H) is fed with methane and steam (16) where it undergoes reforming reaction at elevated temperatures of about 750-850° C. and produces effluent gas (17) comprising of hydrogen, carbon monoxide, carbon dioxide and un-reacted methane and steam. In the HGU Shift reactor (G), the carbon monoxide from Reformer effluent gases (17) and that from ODH process (13) gets converted into hydrogen and carbon dioxide in presence of steam.

The product gases from the HGU shift reactor (18) consisting of hydrogen, carbon dioxide, carbon monoxide, methane with traces of steam and nitrogen are sent to Pressure Swing Adsorption (PSA) section (I) of HGU where pure hydrogen (19) is separated. The off gases from PSA (20) having a typical composition of carbon dioxide 80-95 wt %, carbon monoxide 0.1-5 wt %, methane 0.1-10 wt %, hydrogen 0.1-5 wt % and traces of steam and nitrogen is normally routed to furnace of Reformer reactor as fuel (21). However, the calorific value of this fuel is low due to the presence of high concentration of carbon dioxide (>80 wt %). In the current embodiment, a portion of the PSA off gas (22) is sent to ODH reactor as a carbon dioxide source to supplement the recycle carbon dioxide rich stream (14) coming from the $C_2$ Splitter section (F).

In another embodiment, the present invention is integrated with existing Propylene/Ethylene recovery units (PRU/ERU) or Propylene/Ethylene Separation Units (PSU) of refinery, comprising of De-Butanizer, De-ethanizer, De-methanizer, $C_2$ and $C_3$ splitter. Typically, PRU/ERU exists at downstream of high severity FCC process or Steam cracker process. This integration avoids B, D, E and F sections dedicated to ODH process of FIG. 1, resulting in lower CAPEX and OPEX.

Figure 2:
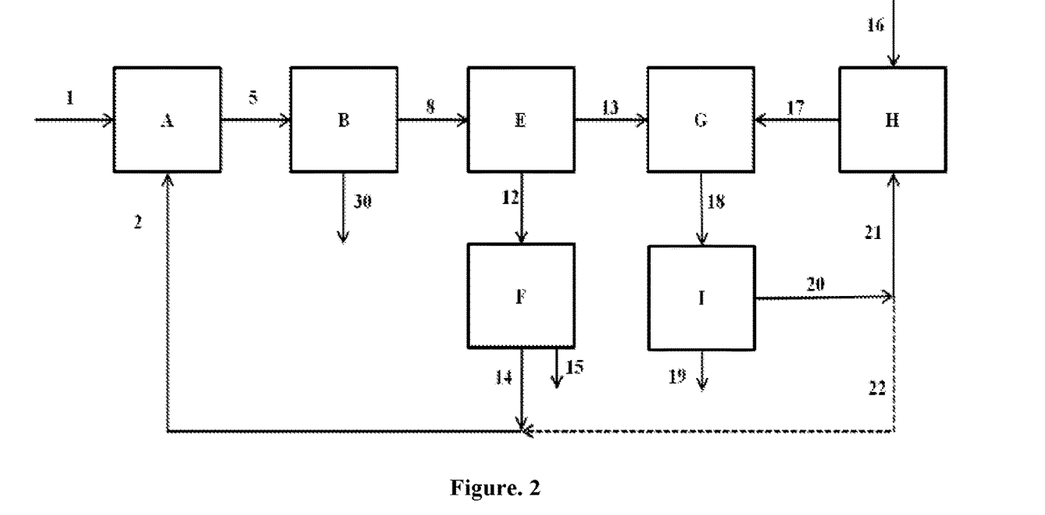
FIG. 2: illustrates the schematic representation of the process for oxidative dehydrogenation of ethane.

One of the embodiments of the present invention is presented in FIG. 2. Ethane (1) and carbon dioxide rich stream (2) are sent to the ODH reactor (A) where the ethane gets converted into ethylene along with minor quantities of other gases such as hydrogen, methane etc. The carbon dioxide acts as a mild oxidizing agent and favors the dehydrogenation reaction. The PSA off gas stream from HGU has a typical composition of carbon dioxide 80-95 wt %, carbon monoxide 0.1-5 wt %, methane 0.1-10 wt %, hydrogen 0.1-5 wt %, and traces of steam and nitrogen (from reformer feed). Thus, the HGU off gas stream is the best suited source of carbon dioxide for ODH process due to high concentration of carbon dioxide and absence of oxygen. Hydrogen & methane in HGU off gas is also helpful in regulating the oxidation state of metals in the catalyst favoring higher alkene selectivity.

The effluent gas (5) from the ODH reactor is sent to the Gas Separation system. The Gas Separation system consists of De-Propanizer section (B), De-Methanizer section (E) and $C_2$ Splitter section (F). The De-Propanizer section (B) separates the ODH effluent gases (5) into (i) $C_2$+ stream (30) consisting of heavy hydrocarbons and (ii) Off gas stream (8) consisting of hydrogen, methane, ethane, ethylene, carbon monoxide and carbon dioxide.

The off gas stream (8) from the De-Propanizer section (B) is sent to De-Methanizer section (E) where this gets separated into two streams (i) a stream consisting of ethane, ethylene and carbon dioxide (12) and (ii) a stream consisting of hydrogen, methane and carbon monoxide (13). The stream consisting of ethane, ethylene and carbon dioxide (12) is sent to the $C_2$ Splitter section (F) where it is separated into petrochemical grade ethylene (15) and a stream rich in ethane and carbon dioxide (14). The stream rich in ethane and carbon dioxide (14) is sent back to the ODH reactor (A) for recycling of ethane and carbon dioxide.

The stream (13) coming from the De-Methanizer section (E) consists of hydrogen (0-5 wt %), methane (0-20 wt %) and carbon monoxide (0-90 wt %) and is sent to the Shift Reactor of HGU (G). This stream (13) gets mixed with the effluent gases (17) from the HGU Reformer Reactor (H). The HGU Reformer reactor (H) is fed with methane and steam (16) where it undergoes reforming reaction at elevated temperatures of about 750-850° C. and produces effluent gas (17) comprising of hydrogen, carbon monoxide, carbon dioxide and un-reacted methane & steam. In the HGU Shift reactor (G), the carbon monoxide from Reformer effluent gases (17) and that from ODH process (13) gets converted into hydrogen and carbon dioxide in presence of steam.

The product gases from the HGU shift reactor (18) consisting of hydrogen (typical composition of 5-20 wt %), carbon dioxide (typical composition of 0-80 wt %) and rest carbon monoxide, methane and steam are sent to Pressure Swing Adsorption (PSA) section (I) of HGU where pure hydrogen (19) is separated. The off gases from PSA (20) having a typical composition of carbon dioxide 80-95 wt %, carbon monoxide 0-4 wt %, methane 0-4 wt %, hydrogen 0-4 wt % and rest steam is normally routed to furnace of Reformer reactor as fuel (21). In the current invention, a portion of the PSA off gas (22) is sent to ODH reactor as a carbon dioxide source to supplement the recycle carbon dioxide rich stream (14) coming from the $C_2$ Splitter section (F).

Figure 3:
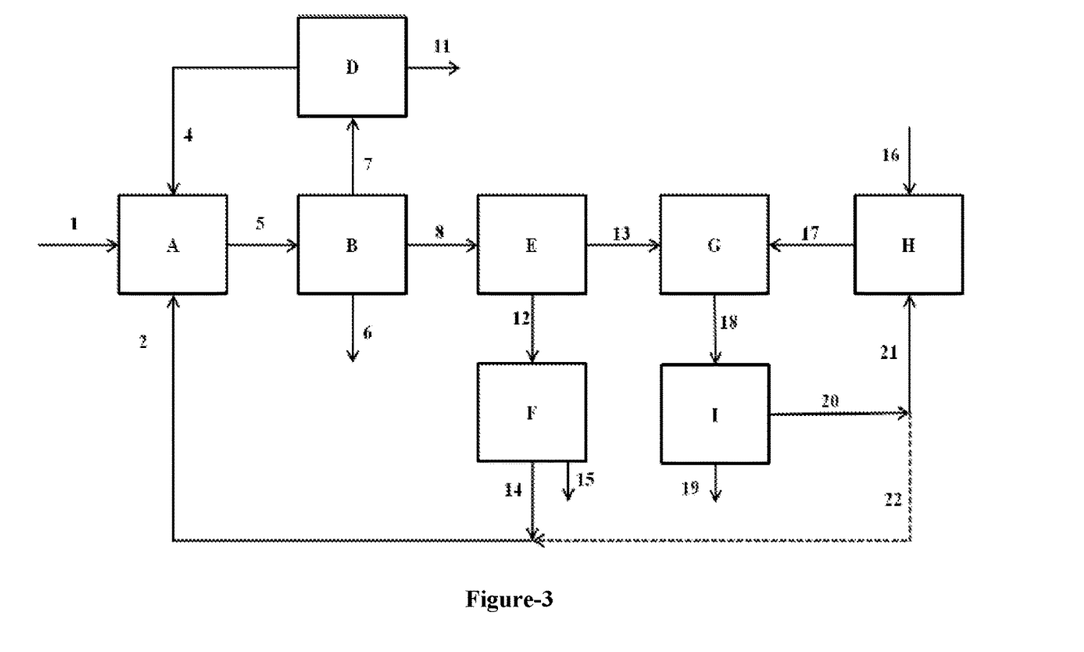
FIG. 3: illustrates the schematic representation of the process for oxidative dehydrogenation of propane.

One of the embodiments of the present invention is presented in FIG. 3. Propane and carbon dioxide rich stream (2) are sent to the ODH reactor (A) where the propane gets converted into propylene along with minor quantities of other gases such as hydrogen, methane, ethylene etc. The carbon dioxide acts as a mild oxidizing agent and favors the dehydrogenation reaction. The PSA off gas stream from HGU has a typical composition of carbon dioxide 80-95 wt %, carbon monoxide 0.1-5 wt %, methane 0.1-10 wt %, hydrogen 0.1-5 wt %, and traces of steam and nitrogen (from reformer feed). Thus, the HGU off gas stream is the best suited source of carbon dioxide for ODH process due to high concentration of carbon dioxide and absence of oxygen. Hydrogen and methane in HGU off gas is also helpful in regulating the oxidation state of metals in the catalyst favoring higher alkene selectivity.

The effluent gas (5) from the ODH reactor is sent to the Gas Separation system. The Gas Separation system consists of De-Propanizer section (B), De-Methanizer section (E), C3 Splitter Section (D) and $C_2$ Splitter section (F). The De-Propanizer section (B) separates the ODH effluent gases (5) into (i) $C_4$+ stream (6) consisting of higher hydrocarbons (ii) $C_3$ stream (7) consisting of propane and propylene and (iii) Off gas stream (8) consisting of hydrogen, methane, ethane, ethylene, carbon monoxide and carbon dioxide.

The $C_3$ stream (7) is separated into petrochemical grade propylene (11) and propane rich stream (4) in a $C_3$ Splitter (D). The propane rich stream (4) is recycled back to the ODH reactor (A) for its further conversion.

The off-gas stream (8) from the De-Propanizer section (B) is sent to De-Methanizer section (E) where this gets separated into two streams (i) a stream consisting of ethane, ethylene and carbon dioxide (12) and (ii) a stream consisting of hydrogen, methane and carbon monoxide (13). The stream consisting of ethane, ethylene and carbon dioxide (12) is sent to the $C_2$ Splitter section (F) where it is separated into petrochemical grade ethylene (15) and a stream rich in ethane and carbon dioxide (14). The stream rich in ethane and carbon dioxide (14) is sent back to the ODH reactor (A) for recycling of ethane and carbon dioxide.

The stream (13) coming from the De-Methanizer section (E) consists of hydrogen (0-5 wt %) methane (0-20 wt %) and carbon monoxide (0-90 wt %) and is sent to the Shift Reactor of HGU (G). This stream (13) gets mixed with the effluent gases (17) from the HGU Reformer Reactor (H). The HGU Reformer reactor (H) is fed with methane and steam (16) where it undergoes reforming reaction at elevated temperatures of about 750-850° C. and produces effluent gas (17) comprising of hydrogen, carbon monoxide, carbon dioxide and un-reacted methane & steam. In the HGU Shift reactor (G), the carbon monoxide from Reformer effluent gases (17) and that from ODH process (13) gets converted into hydrogen and carbon dioxide in presence of steam.

The product gases from the HGU shift reactor (18) consisting of hydrogen (typical composition of 5-20 wt %), carbon dioxide (typical composition of 0-80 wt %) and rest carbon monoxide, methane and steam are sent to Pressure Swing Adsorption (PSA) section (I) of HGU where pure hydrogen (19) is separated. The off gases from PSA (20) having a typical composition of carbon dioxide 80-95 wt %, carbon monoxide 0.1-5 wt %, methane 0.1-10 wt %, hydrogen 0.1-5 wt %, and traces of steam and nitrogen (from reformer feed), is normally routed to furnace of Reformer reactor as fuel (21). However, the calorific value of this fuel is low due to the presence of high concentration of carbon dioxide (>80 wt %). In the current embodiment, a portion of the PSA off gas (22) is sent to ODH reactor as a carbon dioxide source to supplement the recycle carbon dioxide rich stream (14) coming from the $C_2$ Splitter section (F).

This integration of ODH process with HGU have the following benefits:
(1) Production of light olefins with high selectivity as shown in Example 1;
(2) No purification system requirement for carbon dioxide;
(3) No separate hydrogen separation system requirement;
(4) Potential of producing hydrogen from ODH process which otherwise would have been lost as water; and
(5) Reduced capital and operating cost.

In an aspect of the present invention, the present invention discloses an integrated process for catalytic oxidative dehydrogenation (ODH) of alkane(s) and for generation of hydrogen, the process comprising: a) feeding fresh hydrocarbon alkane feed (1) along with carbon dioxide rich stream (2) to ODH reactor (A) where the alkane feed gets converted into alkenes along with minor quantities of hydrogen and methane; b) separating ODH effluent gas (5) from the ODH reactor (A) using a Gas Separation system, wherein the Gas Separation system consists of De-Propanizer section (B), De-Butanizer and $C_4$ Splitter section (C), $C_3$ Splitter section (D), De-Methanizer section (E) and $C_2$ Splitter section (F); c) separating the ODH effluent gases (5) into (i) $C_4$+ stream (6) consisting of $C_4$ alkanes, $C_4$ olefins and higher hydrocarbons; (ii) $C_3$ stream (7) consisting of propane and propylene; and (iii) Off gas stream (8) consisting of hydrogen, methane, ethane, ethylene, carbon monoxide and carbon dioxide using the De-Propanizer section (B); d) separating butanes (3), butene (9) and heavy hydrocarbons (10) from $C_4$+ stream (6) using the De-Butanizer and $C_4$ Splitter section (C) and recycling back the butane (3) to the ODH reactor (A) for further conversion; e) separating the $C_3$ stream (7) into petrochemical grade propylene (11) and propane rich stream (4) using a $C_3$ Splitter (D) and recycling back propane rich stream (4) to the ODH reactor (A) for further conversion; f) routing the Off gas stream (8) from the De-Propanizer section (B) to De-Methanizer section (E), wherein the Off gas stream (8) gets separated into two streams (i) a stream consisting of ethane, ethylene and carbon dioxide (12) and (ii) a stream consisting of hydrogen, methane and carbon monoxide (13); g) routing the stream consisting of ethane, ethylene and carbon dioxide (12) to the $C_2$-Splitter section (F) wherein the stream (12) is separated into petrochemical grade ethylene (15) and a stream rich in ethane and carbon dioxide (14); h) routing the stream rich in ethane and carbon dioxide (14) back to the ODH reactor (A) for recycling of ethane and carbon dioxide; i) routing the stream (13) coming from the De-Methanizer section (E) consisting of hydrogen, methane and carbon monoxide to the Shift Reactor of HGU (G) and mixing the stream (13) with effluent gases (17) coming from Hydrogen Generation Unit (HGU) Reformer Reactor (H); wherein the HGU Reformer reactor (H) is fed with methane, naphtha or other suitable hydrocarbon feed and steam (16) and the hydrocarbon feed and steam (16) undergo reforming reaction at elevated temperatures of about 750-850° C. and produces effluent gas (17) comprising of hydrogen, carbon monoxide, carbon dioxide and un-reacted methane and steam and traces of nitrogen; j) converting the carbon monoxide from the Reformer effluent gases (17) and from the ODH process (13) into hydrogen and carbon dioxide in presence of steam in the HGU Shift reactor (G); k) routing product gases (18) from the HGU shift reactor (G) consisting of hydrogen, carbon dioxide and rest carbon monoxide, methane, steam and nitrogen to Pressure Swing Adsorption (PSA) section (I) of HGU to separate pure hydrogen (19); l) routing Off gases from PSA (20) having a composition of carbon dioxide 80-95 wt %, carbon monoxide 0.1-5 wt %, methane 0.1-10 wt %, hydrogen 0.1-5 wt % and traces of steam and nitrogen to furnace of Reformer reactor (H) as fuel (21); m) routing a portion of the PSA Off gas (22) to the ODH reactor (A) as a carbon dioxide source to supplement the recycle carbon dioxide rich stream (14) coming from the $C_2$ Splitter section (F).

In an aspect of the present invention, the present invention discloses an integrated process for catalytic oxidative dehydrogenation (ODH) of alkane(s) and for generation of hydrogen, the process comprising: a) feeding fresh hydrocarbon alkane feed (1) along with carbon dioxide rich stream (2) to ODH reactor (A) wherein the alkane feed gets converted into alkenes along with minor quantities of hydrogen and methane; b) separating ODH effluent gas (5) from the ODH reactor (A) using a Gas Separation system, wherein the Gas Separation system consists of De-Propanizer section (B), De-Butanizer and $C_4$ Splitter section (C), $C_3$ Splitter section (D), De-Methanizer section (E) and $C_2$ Splitter section (F); c) separating the ODH effluent gases (5) into (i) $C_4$+ stream (6) consisting of $C_4$ alkanes, $C_4$ olefins and higher hydrocarbons; (ii) $C_3$ stream (7) consisting of propane and propylene; and (iii) Off gas stream (8) consisting of hydrogen, methane, ethane, ethylene, carbon monoxide and carbon dioxide using the De-Propanizer section (B); d) separating butanes (3), butene (9) and heavy hydrocarbons (10) from $C_4$+ stream (6) using the De-Butanizer and $C_4$ Splitter section (C) and recycling back the butane (3) to the ODH reactor (A) for further conversion; e) separating the $C_3$ stream (7) into petrochemical grade propylene (11) and propane rich stream (4) using a $C_3$ Splitter (D) and recycling back propane rich stream (4) to the ODH reactor (A) for further conversion; f) routing the Off gas stream (8) from the De-Propanizer section (B) to De-Methanizer section (E), wherein the Off gas stream (8) gets separated into two streams (i) a stream consisting of ethane, ethylene and carbon dioxide (12) and (ii) a stream consisting of hydrogen, methane and carbon monoxide (13); g) routing the stream consisting of ethane, ethylene and carbon dioxide (12) to the $C_2$-Splitter section (F) wherein the stream (12) is separated into petrochemical grade ethylene (15) and a stream rich in ethane and carbon dioxide (14); h) routing the stream rich in ethane and carbon dioxide (14) back to the ODH reactor (A) for recycling of ethane and carbon dioxide; i) routing the stream (13) coming from the De-Methanizer section (E) consisting of hydrogen, methane and carbon monoxide to the Shift Reactor of HGU (G) and mixing the stream (13) with effluent gases (17) coming from Hydrogen Generation Unit (HGU) Reformer Reactor (H), wherein the HGU Reformer reactor (H) is fed with methane, naphtha or other suitable hydrocarbon feed and steam (16) and the hydrocarbon feed and steam (16) undergo reforming reaction at elevated temperatures of about 750-850° C. and produces effluent gas (17) comprising of hydrogen, carbon monoxide, carbon dioxide and un-reacted methane and steam and traces of nitrogen; j) converting the carbon monoxide from the Reformer effluent gases (17) and from the ODH process (13) into hydrogen and carbon dioxide in presence of steam in the HGU Shift reactor (G); k) routing product gases (18) from the HGU shift reactor (G) consisting of hydrogen, carbon dioxide and rest carbon monoxide, methane, steam and nitrogen to Pressure Swing Adsorption (PSA) section (I) of HGU to separate pure hydrogen (19); l) routing Off gases from PSA (20) having a composition of carbon dioxide 80-95 wt %, carbon monoxide 0.1-5 wt %, methane 0.1-10 wt %, hydrogen 0.1-5 wt % and traces of steam and nitrogen to furnace of Reformer reactor (H) as fuel (21); m) routing a portion of the PSA Off gas (22) to the ODH reactor (A) as a carbon dioxide source to supplement the recycle carbon dioxide rich stream (14) coming from the $C_2$ Splitter section (F).

In an aspect of the present invention, the present invention discloses an integrated process for catalytic oxidative dehydrogenation (ODH) of alkane(s) and for generation of hydrogen, the process comprising: a) feeding fresh hydrocarbon alkane feed (1) along with carbon dioxide rich stream (2) to ODH reactor (A) where the alkane feed gets converted into alkenes along with minor quantities of hydrogen and methane; b) separating ODH effluent gas (5) from the ODH reactor (A) using a Gas Separation system, wherein the Gas Separation system consists of De-Propanizer section (B), De-Butanizer and $C_4$ Splitter section (C), $C_3$ Splitter section (D), De-Methanizer section (E) and $C_2$ Splitter section (F); c) separating the ODH effluent gases (5) into (i) $C_4$+ stream (6) consisting of $C_4$ alkanes, $C_4$ olefins and higher hydrocarbons; (ii) $C_3$ stream (7) consisting of propane and propylene; and (iii) Off gas stream (8) consisting of hydrogen, methane, ethane, ethylene, carbon monoxide and carbon dioxide using the De-Propanizer section (B); d) separating butanes (3), butene (9) and heavy hydrocarbons (10) from $C_4$+ stream (6) using the De-Butanizer and $C_4$ Splitter section (C) and recycling back the butane (3) to the ODH reactor (A) for further conversion; e) separating the $C_3$ stream (7) into petrochemical grade propylene (11) and propane rich stream (4) using a $C_3$ Splitter (D) and recycling back propane rich stream (4) to the ODH reactor (A) for further conversion; f) routing the Off gas stream (8) from the De-Propanizer section (B) to De-Methanizer section (E), wherein the Off gas stream (8) gets separated into two streams (i) a stream (12) consisting of ethane, ethylene and carbon dioxide and (ii) a stream (13) consisting of hydrogen, methane and carbon monoxide (13); g) routing the stream (12) consisting of ethane, ethylene and carbon dioxide to the $C_2$-Splitter section (F) wherein the stream (12) is separated into petrochemical grade ethylene (15) and a stream (14) rich in ethane and carbon dioxide; h) routing the stream (14) rich in ethane and carbon dioxide back to the ODH reactor (A) for recycling of ethane and carbon dioxide; i) routing the stream (13) coming from the De-Methanizer section (E) consisting of hydrogen 0-5 wt %, methane 0-20 wt % and carbon monoxide 0-90 wt % to the Shift Reactor of HGU (G) and mixing the stream (13) with effluent gases (17) coming from Hydrogen Generation Unit (HGU) Reformer Reactor (H), wherein the HGU Reformer reactor (H) is fed with a stream (16) comprising of naphtha or other suitable hydrocarbon feed and steam, and the stream (16) undergo reforming reaction at elevated temperatures of about 750-850° C. and produces effluent gas (17) comprising of hydrogen, carbon monoxide, carbon dioxide and un-reacted methane and steam and traces of nitrogen; j) converting the carbon monoxide from the Reformer effluent gases (17) and from the stream (13) into hydrogen and carbon dioxide in presence of steam in the HGU Shift reactor (G); k) routing product gases (18) from the HGU shift reactor (G) consisting of hydrogen, carbon dioxide and rest carbon monoxide, methane, steam and nitrogen to Pressure Swing Adsorption (PSA) of HGU to separate pure hydrogen (19); l) routing Off gases (20) from PSA section (I) having a composition of carbon dioxide 80-95 wt %, carbon monoxide 0.1-5 wt %, methane 0.1-10 wt %, hydrogen 0.1-5 wt % and traces of steam and nitrogen to furnace of HGU Reformer reactor (H) as fuel (21); m) routing a portion of the PSA section (I) Off gas (22) to the ODH reactor (A) as a carbon dioxide source to supplement the recycle carbon dioxide rich stream (14) coming from the $C_2$ Splitter section (F).

PSA off gas composition range will cover the cases of "other hydrocarbon feed" used in hydrogen generation unit.

In an embodiment of the present invention, the fresh hydrocarbon alkane feed (1) is selected from the group consisting of ethane, propane, n-butane and iso-butane or any mixture thereof.

In an embodiment of the present invention, the carbon dioxide rich stream (2) is a PSA off gas stream (22).

In an embodiment of the present invention, conversion of the propane to propylene is 20-40 wt % and selectivity of the propylene is 85-95 wt %.

In an embodiment of the present invention, the ODH reactor (A) is a fixed bed tubular reactor or a fluidized bed reactor or a moving bed reactor or any combination thereof.

In an embodiment of the present invention, the dehydrogenation catalyst comprises of metal oxides, wherein metal in the metal oxide is selected from the group consisting of VB, VIB, VIII and alkali metals group.

In an embodiment of the present invention, molar ratio of the fresh hydrocarbon alkane feed (1) to the carbon dioxide rich stream (2) in step a) is in the range of 0.3-0.8.

In an embodiment of the present invention, gas hourly space velocity (GHSV) of a mixture of the fresh hydrocarbon alkane feed (1) and the carbon dioxide rich stream (2) in step a) is 200-2500 $h^{-1}$.

In an embodiment of the present invention, diluent ($N_2$) concentration in a mixture of the fresh hydrocarbon alkane feed (1) and the carbon dioxide rich stream (2) in step a) is 0.01-30 vol %.

EXAMPLES

Example 1

This example illustrates the performance of ODH catalyst in the presence of HGU PSA off-gas (synthetic mixture comprising of $CO_2$, $CH_4$ and $H_2$). Vanadium based dehydrogenation catalyst was prepared and used in the process. The experiments were conducted in a fixed-bed tubular reactor of 9 mm ID containing 1.618 g catalyst at reaction temperature of 600° C., as measured by the thermocouple located in the catalyst bed. Two experiments were conducted, one using pure propane as feed and pure $CO_2$ (>99%) as co-feed and other using pure propane as feed and synthetic PSA off-gas mixture as co-feed. The molar ratio of propane to $CO_2$ in the feed mixture was 0.5-0.75, gas hourly space velocity (GHSV) of the feed gas was 500-1000 $h^{-1}$ and diluent ($N_2$) concentration in the feed mixture was 5-20 vol %.

The flow rates of inlet gases were controlled by mass flow controllers. The inlet and outlet compositions of gases were analyzed in a Refinery Gas Analyzer equipped with thermal conductivity detector (TCD) and flame ionization detector (FID) at regular intervals. Propane conversion, propylene yield and selectivity were calculated using the formulae given below, and the obtained results are compared in Table 1.

$$\% \text{ Conversion} = \frac{\text{weight of propane(in)} - \text{weight of propane(out)}}{\text{weight of propane(in)}} * 100$$

$$\% \text{ Yield} = \frac{\text{weight of propylene formed}}{\text{weight of propane(in)}} * 100$$

$$\% \text{ Selectivity} = \frac{\text{Propylene yield}}{\text{Propane conversion}} * 100$$

TABLE 1

Experimental Results with Pure $CO_2$ and HGU PSA off-gas

| | Co-feed | |
|---|---|---|
| Attributes | Pure $CO_2$ | Synthetic PSA off-gas mixture |
| Propane conversion (wt %) | 32.6 | 24.8 |
| Propylene yield (wt %) | 24.8 | 22.9 |
| Propylene selectivity (wt %) | 76.0 | 92.3 |

Propylene selectivity in the presence of HGU PSA off-gas mixture increased by 21.5% when compared with that of pure carbon dioxide as co-feed.

The invention claimed is:

1. An integrated process for catalytic oxidative dehydrogenation (ODH) of alkane(s) and for generation of hydrogen, the process comprising:
   a) feeding a fresh hydrocarbon alkane feed along with a carbon dioxide rich stream to an ODH reactor comprising of dehydrogenation catalyst, where the alkane feed gets converted into alkenes and producing an effluent gas comprising of hydrogen, methane, carbon monoxide, carbon dioxide, water and unreacted alkanes;
   b) separating ODH effluent gas from the ODH reactor in a Gas Separation system, wherein the Gas Separation system consists of a De-Propanizer section, a De-Butanizer and $C_4$ Splitter section, a $C_3$ Splitter section, a De-Methanizer section and a $C_2$ Splitter section;
   c) separating the ODH effluent gases into:
      (i) a $C_{4+}$ stream consisting of $C_4$ alkanes, $C_4$ olefins and higher hydrocarbons;
      (ii) a $C_3$ stream consisting of propane and propylene; and
      (iii) an Off gas stream consisting of hydrogen, methane, ethane, ethylene, carbon monoxide and carbon dioxide in the De-Propanizer section;
   d) separating butanes, butene and heavy hydrocarbons from the $C_{4+}$ stream in the De-Butanizer and the $C_4$ Splitter section and recycling back the butane to the ODH reactor for further conversion;
   e) separating the $C_3$ stream into petrochemical grade propylene and a propane rich stream in a $C_3$ Splitter and recycling back the propane rich stream to the ODH reactor for further conversion;
   f) routing the Off gas stream from the De-Propanizer section to De-Methanizer section, wherein the Off gas stream gets separated into two streams (i) a stream consisting of ethane, ethylene and carbon dioxide and (ii) a stream consisting of hydrogen, methane and carbon monoxide;
   g) routing the stream consisting of ethane, ethylene and the carbon dioxide to the $C_2$-Splitter section wherein the stream is separated into petrochemical grade ethylene and a stream rich in ethane and carbon dioxide;
   h) routing the stream rich in ethane and carbon dioxide back to the ODH reactor for recycling of ethane and carbon dioxide;
   i) routing the stream coming from the De-Methanizer section consisting of hydrogen, methane and carbon monoxide to a Hydrogen Generation Unit (HGU) Shift Reactor and mixing the stream with effluent gases coming from a Hydrogen Generation Unit (HGU) Reformer Reactor, wherein the HGU Reformer reactor is fed with methane, naphtha or other suitable hydrocarbon feed and steam and the hydrocarbon feed and steam undergo reforming reaction at elevated temperatures of about 750-850° C. and produces effluent gas including hydrogen, carbon monoxide, carbon dioxide and un-reacted methane and steam and traces of nitrogen;

j) converting the carbon monoxide from the effluent gases and from the stream into hydrogen and carbon dioxide in presence of steam in the HGU Shift reactor, k) routing product gases from the HGU shift reactor consisting of hydrogen, carbon dioxide and rest carbon monoxide, methane, steam and nitrogen to a Pressure Swing Adsorption (PSA) section of the HGU shift reactor to separate pure hydrogen;

l) routing a portion of off gases from the PSA having a composition of carbon dioxide 80-95 wt %, carbon monoxide 0.1-5 wt %, methane 0.1-10 wt %, hydrogen 0.1-5 wt % and traces of steam and nitrogen to furnace of the HGU reformer reactor as fuel; and m) routing remaining portion of the PSA Off gas to the ODH reactor as a carbon dioxide source to supplement the recycle carbon dioxide rich stream coming from the $C_2$ Splitter section.

2. The process as claimed in claim 1, wherein the fresh hydrocarbon alkane feed is selected from the group consisting of ethane, propane, n-butane and iso-butane or any mixture thereof.

3. The process as claimed in claim 1, wherein the carbon dioxide rich stream is a PSA off gas stream.

4. The process as claimed in claim 2, wherein conversion of the propane to propylene is 20-40 wt % and selectivity of the propylene is 85-95 wt %.

5. The process as claimed in claim 1, wherein the ODH reactor is a fixed bed tubular reactor or a fluidized bed reactor or a moving bed reactor or any combination thereof.

6. The process as claimed in claim 1, wherein the dehydrogenation catalyst comprises of metal oxides, wherein metals in the metal oxides are selected from the group consisting of VB, VIB, VIII and alkali metals group.

7. The process as claimed in claim 1, wherein molar ratio of the fresh hydrocarbon alkane feed to the carbon dioxide fed to ODH reactor in step a) is in the range of 0.3-0.8.

8. The process as claimed in claim 1, wherein gas hourly space velocity (GHSV) of a mixture of the fresh hydrocarbon alkane feed and the carbon dioxide rich stream in step a) is 200-2500 $h^{-1}$.

9. The process as claimed in claim 1, diluent ($N_2$) concentration in a mixture of the fresh hydrocarbon alkane feed and the carbon dioxide rich stream in step a) is 0.01-30 vol %.

* * * * *